US009414845B2

(12) United States Patent
Boykin

(10) Patent No.: US 9,414,845 B2
(45) Date of Patent: Aug. 16, 2016

(54) MICRO-SAW BLADE FOR BONE-CUTTING SURGICAL SAWS

(71) Applicant: Medtronic PS Medical, Inc., Louisville, CO (US)

(72) Inventor: Christopher M. Boykin, Athens, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 48 days.

(21) Appl. No.: 14/581,328

(22) Filed: Dec. 23, 2014

(65) Prior Publication Data

US 2015/0112347 A1 Apr. 23, 2015

Related U.S. Application Data

(62) Division of application No. 12/136,956, filed on Jun. 11, 2008, now Pat. No. 8,920,424.

(51) Int. Cl.
*A61B 17/14* (2006.01)
*A61C 3/12* (2006.01)
(Continued)

(52) U.S. Cl.
CPC ............... *A61B 17/148* (2013.01); *A61B 17/14* (2013.01); *A61B 17/141* (2013.01);
(Continued)

(58) Field of Classification Search
CPC .... A61B 17/148; A61B 17/14; A61B 17/141; Y10T 83/9319; Y10T 83/9473; B27B 19/006; B23D 51/10; B23D 61/006
USPC .................. 30/122, 351, 355; 83/835, 698.11
See application file for complete search history.

(56) References Cited

U.S. PATENT DOCUMENTS 384,979 A * 6/1888 Hurd .................... B23D 61/025
83/835
2,138,862 A * 12/1938 Johnston ................ A61B 17/14
74/44
(Continued)

FOREIGN PATENT DOCUMENTS

DE 4036904 C1 5/1992
EP 0554929 A1 8/1993
(Continued)

OTHER PUBLICATIONS

Australian Office Action mailed Apr. 10, 2013 for Australian Patent Application No. 2009257762.
(Continued)

*Primary Examiner* — Christian Sevilla
(74) *Attorney, Agent, or Firm* — Harness, Dickey

(57) ABSTRACT

A surgical cutting blade for cutting bone material when the blade is coupled to a hand-held surgical saw having protrusions extending therefrom that interface with the cutting blade. The cutting blade includes a distal end comprising a plurality of cutting teeth and a shank portion adjacent the distal end. It also includes a proximal end adjacent the shank portion. The proximal end is shaped to attach to the surgical saw and includes an upper substantially planar surface and a lower substantially planar surface and a side edge extending between the upper and lower planar surfaces. The side edge at least in part defines an outer perimeter extending about the proximal end. The outer perimeter includes a plurality of indentations forming openings configured to receive and interface with the protrusions of the surgical saw in a manner that the protrusions cooperatively impart motion to drive the blade.

20 Claims, 11 Drawing Sheets

(51) Int. Cl.
   *B23D 61/00* (2006.01)
   *B23D 61/12* (2006.01)
   *B27B 5/32* (2006.01)
   *B27B 19/00* (2006.01)
   *B27B 33/02* (2006.01)
   *A61B 17/16* (2006.01)

(52) U.S. Cl.
   CPC .............. *A61B 17/1613* (2013.01); *A61C 3/12* (2013.01); *B23D 61/006* (2013.01); *B23D 61/125* (2013.01); *B27B 5/32* (2013.01); *B27B 19/006* (2013.01); *B27B 33/02* (2013.01)

(56) References Cited

U.S. PATENT DOCUMENTS

| | | | |
|---|---|---|---|
| 2,310,409 A | 2/1943 | Ellman | |
| 2,606,366 A * | 8/1952 | Stevens | A61C 3/02 188/268 |
| 2,685,734 A * | 8/1954 | Klein | A22B 5/0047 30/144 |
| 3,292,237 A | 12/1966 | Fisher | |
| 3,554,197 A | 1/1971 | Dobbie | |
| 3,678,934 A | 7/1972 | Warfield et al. | |
| 3,905,105 A * | 9/1975 | Tuke | A61B 17/14 30/393 |
| 3,905,374 A * | 9/1975 | Winter | A61B 17/14 30/166.3 |
| 3,927,893 A | 12/1975 | Dillon et al. | |
| 3,943,934 A * | 3/1976 | Bent | A61B 17/14 30/339 |
| 3,952,412 A | 4/1976 | Rhodes | |
| 3,977,289 A * | 8/1976 | Tuke | A61B 17/14 30/392 |
| 3,978,862 A | 9/1976 | Morrison | |
| 4,020,555 A * | 5/1977 | Hedrick | A61B 17/14 279/89 |
| 4,106,181 A | 8/1978 | Mattchen | A61B 17/14 279/77 |
| 4,386,609 A * | 6/1983 | Mongeon | A61B 17/14 30/339 |
| 4,513,742 A * | 4/1985 | Arnegger | A61B 17/14 30/350 |
| 4,584,999 A | 4/1986 | Arnegger | |
| 4,617,930 A | 10/1986 | Saunders | |
| 4,716,881 A | 1/1988 | Steere | |
| 4,739,557 A | 4/1988 | Wagner | |
| 4,768,504 A | 9/1988 | Ender | |
| 5,002,555 A | 3/1991 | Petersen | |
| 5,058,273 A * | 10/1991 | Streger | B23D 51/10 30/164.9 |
| 5,092,869 A | 3/1992 | Waldron | |
| 5,122,142 A | 6/1992 | Pascaloff | |
| 5,133,728 A | 7/1992 | Petersen | |
| 5,135,533 A | 8/1992 | Petersen et al. | |
| 5,178,626 A | 1/1993 | Pappas | |
| D337,160 S | 7/1993 | Evans | |
| 5,263,972 A * | 11/1993 | Evans | A61B 17/14 30/339 |
| 5,265,343 A | 11/1993 | Pascaloff | |
| D343,247 S | 1/1994 | Walen | |
| 5,306,285 A | 4/1994 | Miller et al. | |
| D348,194 S | 6/1994 | Tanis | |
| 5,366,312 A * | 11/1994 | Raines | A61B 17/14 30/340 |
| D353,888 S | 12/1994 | Raines | |
| 5,382,249 A * | 1/1995 | Fletcher | A61B 17/14 606/176 |
| 5,403,318 A | 4/1995 | Boehringer et al. | |
| D360,946 S | 8/1995 | Goris | |
| D361,029 S | 8/1995 | Goris | |
| 5,439,472 A | 8/1995 | Evans et al. | |
| D362,065 S | 9/1995 | Goris | |
| 5,468,247 A | 11/1995 | Matthai et al. | |
| 5,489,285 A | 2/1996 | Goris | |
| 5,507,763 A | 4/1996 | Petersen et al. | |
| 5,554,165 A | 9/1996 | Raitt et al. | |
| 5,569,257 A * | 10/1996 | Arnegger | A61B 17/14 30/350 |
| 5,658,304 A | 8/1997 | Lim | |
| D385,164 S | 10/1997 | Hutchins et al. | |
| 5,676,680 A | 10/1997 | Lim | |
| 5,694,693 A | 12/1997 | Hutchins et al. | |
| 5,697,158 A | 12/1997 | Klinzing et al. | |
| 5,702,415 A | 12/1997 | Matthai et al. | |
| 5,729,904 A | 3/1998 | Trott | |
| 5,735,866 A * | 4/1998 | Adams | A61B 17/14 30/339 |
| D394,315 S | 5/1998 | Fisher | |
| 5,839,196 A | 11/1998 | Trott | |
| 5,846,244 A * | 12/1998 | Cripe | A61B 17/14 30/166.3 |
| D404,485 S | 1/1999 | Hutchins et al. | |
| D405,177 S | 2/1999 | Hutchins et al. | |
| 5,870,828 A * | 2/1999 | Polites | B26B 5/001 30/151 |
| D406,223 S | 3/1999 | Tran | |
| RE36,269 E | 8/1999 | Wright | |
| 5,941,891 A | 8/1999 | Walen | |
| 6,007,541 A | 12/1999 | Scott | |
| 6,022,353 A * | 2/2000 | Fletcher | A61B 17/14 606/79 |
| 6,045,564 A | 4/2000 | Walen | |
| 6,113,618 A | 9/2000 | Nic | |
| 6,113,619 A | 9/2000 | Pascaloff | |
| 6,302,406 B1 | 10/2001 | Ventura | |
| D455,490 S | 4/2002 | Pascaloff | |
| D459,805 S | 7/2002 | Pascaloff | |
| 6,503,253 B1 | 1/2003 | Fletcher et al. | |
| 6,656,186 B2 | 12/2003 | Meckel | |
| 6,723,101 B2 | 4/2004 | Fletcher et al. | |
| D489,823 S | 5/2004 | Fisher et al. | |
| D492,412 S | 6/2004 | Desoutter et al. | |
| 6,860,886 B1 * | 3/2005 | Lee | A61B 17/148 606/82 |
| 6,865,813 B2 * | 3/2005 | Pollak | B24B 23/04 30/166.3 |
| 6,896,679 B2 * | 5/2005 | Danger | A61B 17/14 606/178 |
| 7,001,403 B2 | 2/2006 | Hausmann et al. | |
| 7,003,888 B2 | 2/2006 | Bigden et al. | |
| 7,040,023 B2 | 5/2006 | Nemazi et al. | |
| 7,189,239 B2 | 3/2007 | Fisher et al. | |
| 8,920,424 B2 * | 12/2014 | Boykin | A61B 17/14 606/82 |
| 8,939,981 B1 * | 1/2015 | Anderson | A61B 17/148 606/79 |
| 2001/0041524 A1 * | 11/2001 | Steiger | B23D 61/006 451/356 |
| 2002/0116023 A1 | 8/2002 | Fletcher et al. | |
| 2002/0133186 A1 * | 9/2002 | Kullmer | B23D 61/006 606/178 |
| 2003/0032971 A1 | 2/2003 | Hausmann et al. | |
| 2003/0172498 A1 | 9/2003 | Polzin et al. | |
| 2003/0199880 A1 * | 10/2003 | Meckel | A61B 17/14 606/82 |
| 2004/0138668 A1 | 7/2004 | Fisher et al. | |
| 2004/0138670 A1 * | 7/2004 | Metzger | A61B 17/141 606/88 |
| 2004/0154133 A1 * | 8/2004 | Polzin | B25F 5/006 16/430 |
| 2004/0243136 A1 * | 12/2004 | Gupta | A61B 17/14 606/82 |
| 2005/0113840 A1 * | 5/2005 | Metzger | A61B 17/157 606/88 |
| 2005/0210686 A1 * | 9/2005 | Ritter | B23D 51/10 30/392 |
| 2006/0009796 A1 | 1/2006 | Carusillo et al. | |
| 2006/0123959 A1 | 6/2006 | Bocast | |
| 2006/0142774 A1 * | 6/2006 | Metzger | A61B 17/155 606/79 |
| 2006/0206100 A1 | 9/2006 | Eskridge et al. | |

(56) References Cited

U.S. PATENT DOCUMENTS

| | | |
|---|---|---|
| 2007/0083209 A1 | 4/2007 | Schenberger et al. |
| 2008/0119860 A1* | 5/2008 | McCarthy ............ A61B 17/148 606/87 |
| 2010/0292701 A1* | 11/2010 | Fisher .................... A61B 17/14 606/82 |

FOREIGN PATENT DOCUMENTS

| | | |
|---|---|---|
| JP | 2008505699 A | 2/2008 |
| JP | 2011-512624 A | 4/2011 |
| WO | WO-9513020 A1 | 5/1995 |
| WO | WO-9710765 A1 | 3/1997 |
| WO | WO-2006017066 A2 | 2/2006 |
| WO | WO-2007041027 A2 | 4/2007 |

OTHER PUBLICATIONS

Australian Office Action mailed May 5, 2014 for Australian Patent Application No. 2009257762.

Chinese Office Action mailed Aug. 31, 2012 for China Patent Application No. 200980128816.X.

Japanese Office Action mailed May 1, 2014 for JP Application No. 2011-513548 corresponding to PCT/US2009/045378.

* cited by examiner

MICRO-SAW BLADE FOR BONE-CUTTING SURGICAL SAWS

CROSS-REFERENCE TO RELATED APPLICATIONS

This application is a divisional of U.S. patent application Ser. No. 12/136,956 filed on Jun. 11, 2008. The entire disclosure of the above application is incorporated herein by reference.

FIELD

The present disclosure relates to a bone-cutting surgical system, and more particularly, to a micro-saw blade suitable for use with a surgical cutting saw.

BACKGROUND

This section provides background information related to the present disclosure which is not necessarily prior art.

Bone-cutting surgical saws, such as sagittal or oscillating type surgical saws, cut most effectively at very high speeds, such as for example, 10000-40000 cycles per minute. These high speeds introduce high levels of vibration and can cause blade wander during a cut. Accordingly, blade cuts typically have a thickness considerably greater than the width of the actual blade. For example, a cutting blade having a 0.015 inch thickness may be unable to cut a groove having a width of less than 0.030 inch. In addition, because the saws operate at such high speeds, the excessive vibration can quickly fatigue a surgeon's hand or wrist. As fatigue sets in, maintaining the same preciseness and accuracy may become more difficult.

A contributing problem is the way the blade attaches to the saw. Conventional systems use pins located close to the centerline of the blade attachment portion, resulting in a short moment arm for driving the blade. Accordingly, during irregular cutting, such as a while making a curved cut or a cut not along the path of the normal oscillating path of the saw blade, the blade can become dislodged, possibly causing some blade loosening. This can result in cuts having a width considerably larger than the blade width.

The devices disclosed herein overcome one or more of short-comings in the prior art.

SUMMARY

This section provides a general summary of the disclosure, and is not a comprehensive disclosure of its full scope or all of its features.

In one exemplary aspect, the present disclosure is directed to a surgical cutting blade for cutting bone material when the blade is coupled to a hand-held surgical saw having protrusions extending therefrom that interface with the cutting blade. The cutting blade includes a distal end comprising a plurality of cutting teeth and a shank portion adjacent the distal end. It also includes a proximal end adjacent the shank portion. The proximal end is shaped to attach to the surgical saw and includes an upper substantially planar surface and a lower substantially planar surface and a side edge extending between the upper and lower planar surfaces. The side edge at least in part defines an outer perimeter extending about the proximal end. The outer perimeter includes a plurality of indentations forming openings configured to receive and interface with the protrusions of the surgical saw in a manner that the protrusions cooperatively impart motion to drive the blade.

In another exemplary aspect, the present disclosure is directed to a surgical cutting blade for cutting bone material when the blade is coupled to a hand-held surgical saw having protrusions extending therefrom that interface with the cutting blade. The cutting blade includes a distal end comprising a plurality of cutting teeth and a shank portion adjacent the distal end. The blade also includes a proximal end adjacent the shank portion. The proximal end is shaped to attach to the surgical saw and includes an upper substantially planar surface and a lower substantially planar surface. The proximal end also includes a perimeter edge and a centrally disposed slot formed therein. The slot defining an inner edge. The proximal end also includes a plurality of openings configured to receive and interface with the protrusions of the surgical saw in a manner that the protrusions cooperatively impart motion to drive the blade. The openings are disposed closer to the perimeter edge than the inner edge.

In another exemplary aspect, the present disclosure is directed to a cutting blade set for cutting bone material when the blade is coupled to a hand-held surgical saw having protrusions extending therefrom that selectively interface with each blade of the cutting blade set. The cutting blade set includes a plurality of cutting blades. Each blade of the plurality of cutting blades includes a distal end comprising a plurality of cutting teeth, the distal end of each cutting blade of the plurality of cutting blades having a different thickness, and includes a shank portion adjacent the distal end. Each blade also includes a proximal end adjacent the shank portion. The proximal end is sized and shaped to interface with the surgical saw. The proximal end of each cutting blade of the plurality of cutting blades has substantially the same thickness.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Generally, the present disclosure relates to a bone cutting surgical system including a hand-held, high-speed, bone-cutting surgical saw, such as a sagittal or oscillating saw, and a cutting micro-saw blade. The saw includes a collet assembly with protruding pins or nubs that mesh with or extend into openings on the cutting blade, thereby securing the blade in place in the collet assembly. In order to minimize the moment forces on the interior of the blade when the blade is rotating, the protrusions on the collet assembly and the openings on the saw blade are placed toward the exterior perimeter of the collet assembly and the exterior perimeter of the saw blade. In one embodiment, the openings are notches formed along the exterior edge of the saw blade. By moving moment forces toward the exterior of the saw blade, blade vibration may be reduced. Reducing vibration increases cutting accuracy, which can reduce patient trauma and speed recovery time, as well as reduce surgeon fatigue. In some embodiments, the micro-saw blades include a dampening overmold that interfaces with the collet assembly. This too may reduce blade vibration. In addition, the overmold may assist with blade identification.

Figure 1:
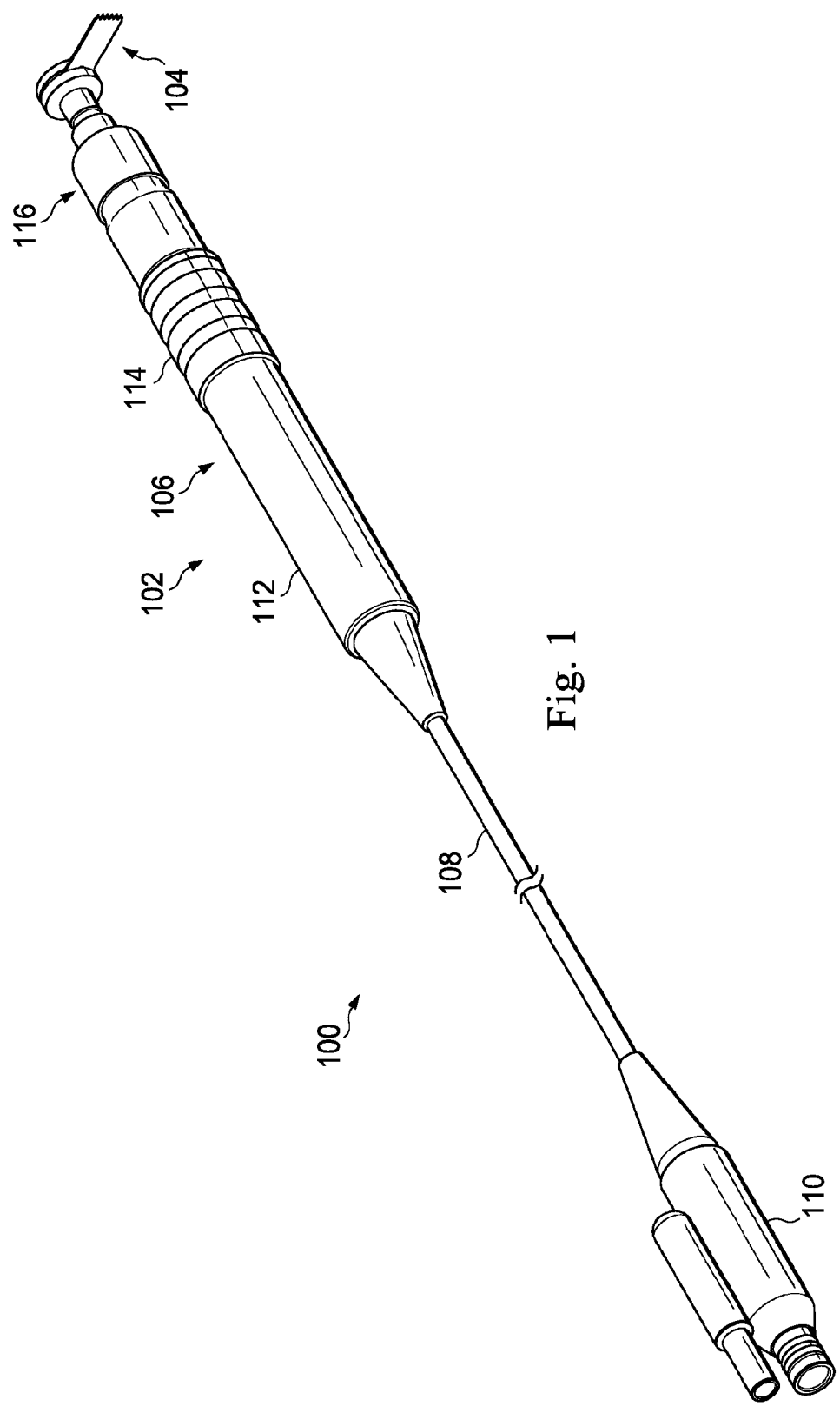
FIG. 1 is an illustration of an exemplary oscillating bone-cutting surgical system.
Figure 2:
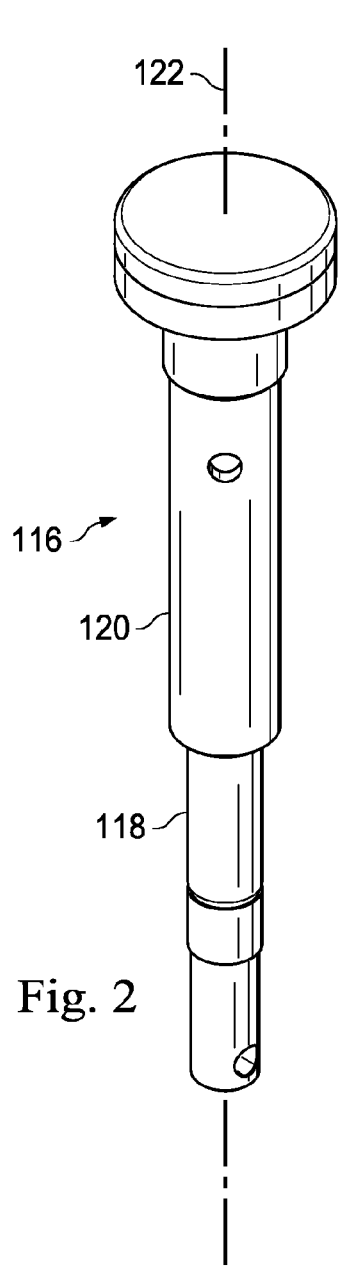
FIG. 2 is an illustration of an exemplary collet assembly from the surgical system of FIG. 1.

Turning now to FIG. 1, the present disclosure is directed to a bone-cutting surgical system 100 including a surgical saw 102 and a selectively removable micro-saw blade 104. The surgical saw 102 includes a hand-piece 106, a cord 108, and a connector 110 configured to removably couple with a power source. The connector 110 is merely exemplary, and it should be apparent to one skilled in the art that any suitable connector may be used, and in some embodiments, the cord 108 itself may be coupled to the power source without the use of a connector. Additional contemplated embodiments include a power source as a part of the hand-piece 106, such as a battery powered hand-piece.

The hand-piece 106 includes a motor assembly 112, a grip 114, and a collet assembly 116. In some embodiments, the motor assembly 112 is housed within the grip 114, while in other embodiments, it is disposed adjacent to the grip 114. It is contemplated that any suitable system for controlling the surgical saw 102 may be used. For example, some embodiments include a trigger system disposed on the hand-piece 106 to provide hand-control of the cutting speed, or alternatively, a foot pedal associated with the hand-piece 106 through the power source to provide the controlling inputs. Other control systems also are contemplated.

FIGS. 2-5 show a portion of the exemplary collet assembly 116. The collet assembly 116 secures the saw blade 104 to the surgical saw 104 and transfers a driving force from the motor to the blade. In this embodiment, it includes a driving shaft 118 and a sleeve 120 defining a longitudinal collet axis 122. The sleeve 120 receives and extends about the driving shaft 118 and is axially movable along the collet axis 122 relative to the driving shaft 118, enabling selective coupling with the blade 104.

Figure 3:
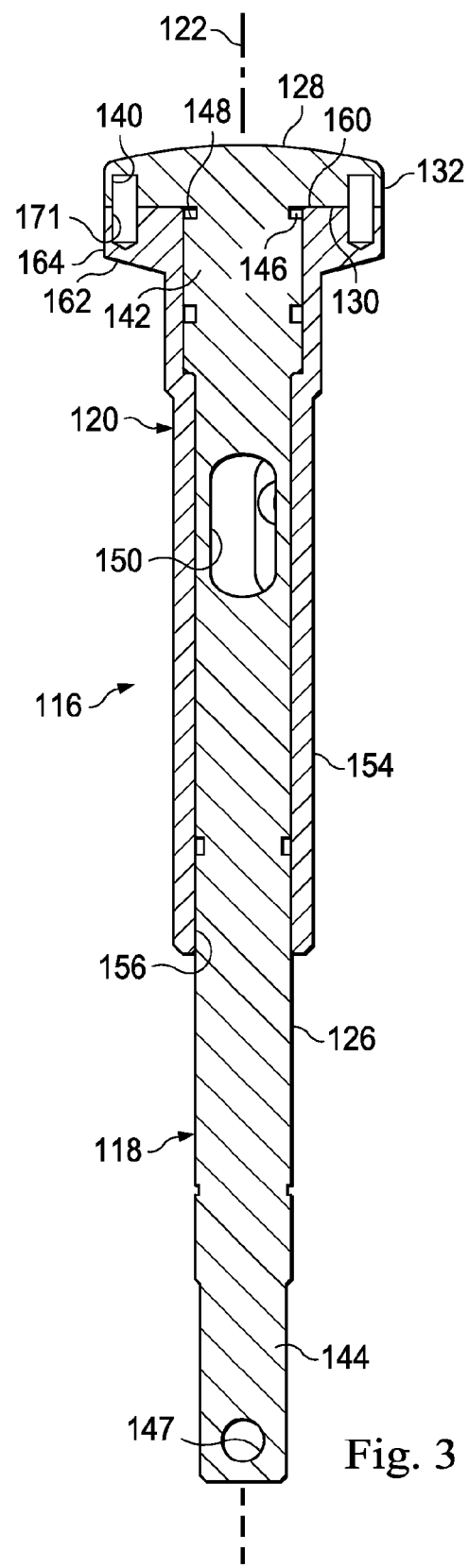
FIG. 3 is an illustration of a cross-section of the exemplary collet assembly of FIG. 2.
Figure 4:
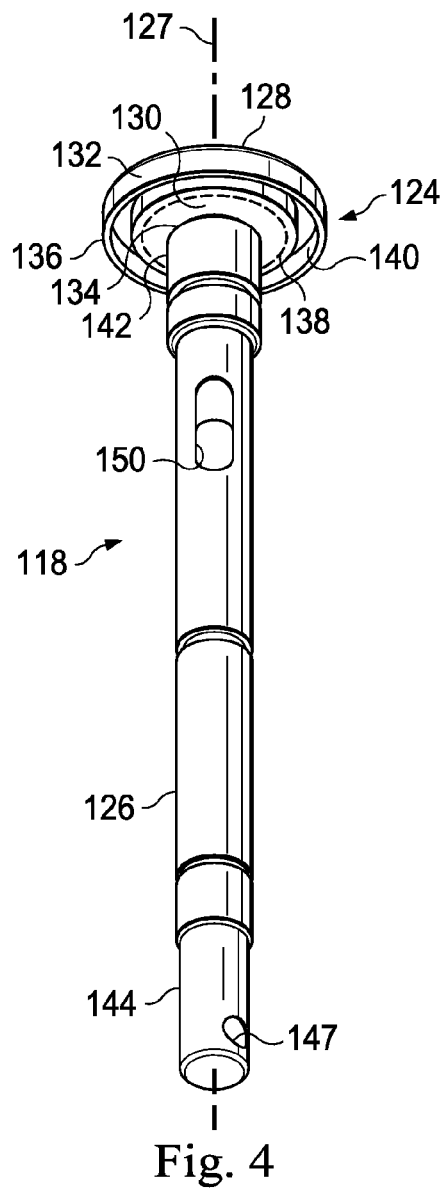
FIG. 4 is an illustration of an exemplary driving shaft of the collet assembly of FIG. 2.

The driving shaft 118 is shown in greater detail in FIGS. 3 and 4. Here, the driving shaft includes a head 124 forming a distal end of the driving shaft and a shank 126 extending proximally from the head 124. These together define a shaft axis 127 (FIG. 4) extending longitudinally through the shaft.

Referring to FIGS. 3 and 4, the head 124 includes a distally facing outer surface 128, a proximally facing blade contacting surface 130 adjacent the shank 126, and an outer perimeter 132 extending therebetween. The blade contacting surface 130 includes an inner edge 134, which in this embodiment is defined where the shank 126 and the blade contacting surface 130 meet. It also includes an outer edge 136, which in this embodiment is defined where the outer perimeter 132 and the blade contacting surface 130 meet. These inner and outer edges 134, 136 define a reference mid-line 138 half-way between them on the blade contacting surface 130.

In this embodiment, the blade contacting surface 130 includes a receiving opening formed therein as a receiving recess 140 for receiving one or more protrusions to be discussed below relative to the sleeve 120. Here, the receiving recess 140 is formed as a single groove concentric about the shaft axis 127 and disposed closer to the outer perimeter 132 than to the shank 126. Accordingly, as shown in FIG. 4, the receiving recess 140 is offset from the mid-line 138 defined by the inner and outer edges 134, 136 of the blade contacting surface 130. In the example shown, the outermost edge of the receiving recess 140 (edge closest to the outer perimeter 132) is located toward the outer edge 136 at least half of the distance between the mid-line 138 and the outer edge 136. Said another way, the outermost edge of the receiving recess 140 is located toward the outer edge 136 at least three quarters or 75% of the distance from the inner edge 134 to the outer edge 136. In some embodiments, the outermost edge of the receiving recess is closer to 80% of the distance between the inner edge 134 and the outer edge 136. In the embodiment shown, the inner most edge of the receiving recess 140 (edge closest to the shank 126) is likewise located more than half the distance toward the outermost edge 136 so that the entire receiving recess 140 is disposed outwardly from the midline 138, or more than half of the distance of the inner edge 134 to the outer edge 136.

Furthermore, in the example of FIG. 4, the outermost edge of the receiving recess 140 is disposed toward the outer edge 136 more than 80% of the distance from the shaft axis 127 to the outer edge 136, and in some embodiments, more than 90% of the distance from the shaft axis 127 to the outer edge 136.

The shank 126 includes a distal end 142 either connected to or integral with the head 124 and a proximal end 144. At the distal end 142, the shank includes a blade receiving radial groove or recess 146 (FIG. 3). The groove 146 is formed such that the blade contacting surface 130 of the head 124 forms one side of the groove 146 while the opposing side is formed by a shoulder portion 148 (FIG. 3) of the shank 126. In the embodiment shown, the groove 146 is formed with a circular diameter sized to mate with and receive a portion of the saw blade 104. However, in other embodiments, the groove 146 is non-circular, and may be formed, for example, of a series of flat surfaces or may be formed of, for example, two grooves formed into opposing sides of the shank 126. An axially elongated slot 150 extends through the shank 126. This can receive a pin (not shown) connecting the shank 126 to the sleeve 120 while still permitting limited axial sliding between the sleeve 120 and shank 126. In this embodiment, the proximal end 144 includes a motor coupling feature 147 shown as a pin-receiving through passage that connects either directly or cooperatively to the motor to provide the cutting oscillation required.

Figure 5:
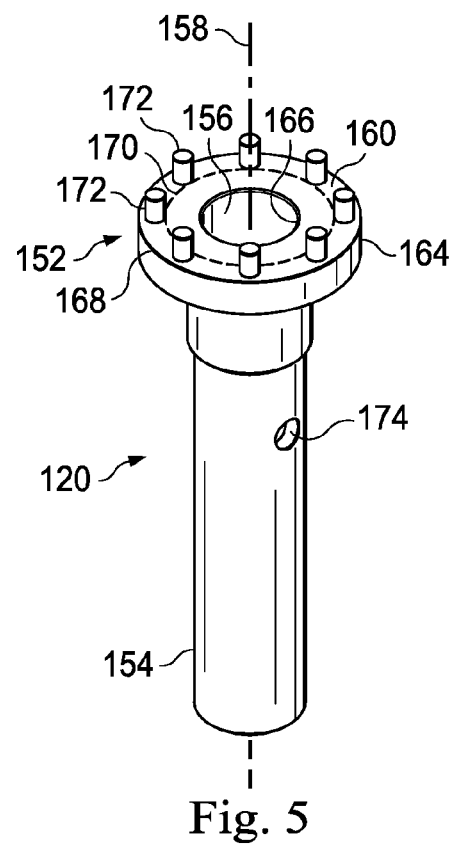
FIG. 5 is an illustration of an exemplary sleeve of the collet assembly of FIG. 2.

FIGS. 3 and 5 show the sleeve 120 in greater detail. The sleeve 120, like the driving shaft 118, includes a head 152 and a shank 154, but is formed with a central bore 156 sized to receive the shank 126 of the driving shaft 118 as shown best in FIG. 3. The sleeve 120 defines a sleeve axis 158 shown in FIG. 5. The head 152 includes a substantially planar distally facing blade contacting surface 160, a proximally facing surface 162, and an outer perimeter 164. In this embodiment, the sleeve outer perimeter 164 is sized to have substantially the same diameter as the driving shaft outer perimeter 132. Further, as shown in FIG. 3, the distally facing blade contacting surface 160 of the sleeve 120 faces the proximally facing blade contacting surface 130 of the driving shaft 118.

The distally facing blade contacting surface 160 includes an inner edge 166, which in this embodiment is defined where the central bore 156 and the distally facing blade contacting surface 160 meet. It also includes an outer edge 168, which in this embodiment is defined where the outer perimeter 164 and the distally facing blade contacting surface 160 meet. These inner and outer edges 166, 168 define a reference midline 170 extending half-way between them on the distally facing blade contacting surface 160.

Referring now to FIG. 5, the distally facing blade contacting surface 160 of the sleeve 120 includes a plurality of protrusions 172 formed thereon. These are symmetrically disposed about the sleeve axis 158 and are configured to interface with the saw blade 104, as is further discussed below. Here, the sleeve 120 includes eight protrusions extending therefrom, spaced apart about the sleeve axis 158. It is contemplated that more or fewer protrusions may be present. The protrusions 172 may be integrally formed with sleeve 120 or, for manufacturing convenience, may be separate components fit, such as with an interference fit, into receiving ports 171 (shown in FIG. 3) formed in the distally facing blade contacting surface 160. For clarity, the protrusions 172 are not shown in FIG. 3, but are shown in FIG. 5. In this embodiment, these protrusions 172 are formed of cylindrical pins extending from the substantially planar distally facing blade contacting surface 160. In other examples however, the protrusions 172 have a square, rectangular, triangular or diamond-shaped cross-section. Protrusions of other shapes are also contemplated.

The protrusions 172 are disposed offset from the mid-line 170 on the distally facing blade contacting surface 160. In the example shown, the protrusions 172 are disposed so that the outermost portion of the protrusions (portion of protrusion closest to the perimeter 164) is located toward the outer edge 1688 at least half of the distance between the midline 138 and the outer edge 168. Said another way, the outermost portions of the protrusions 172 are located toward the outer edge 168 at least three quarters or 75% of the distance from the inner edge 166 to the outer edge 168. In some embodiments, the outermost portions of the protrusions 172 are closer to 80% of the distance between the mid-line 170 and the outer edge 168.

In the embodiment shown, the inner most portions of the protrusions 172 (portions closest to the inner edge 166) are likewise located toward the outermost edge 136 so that the entire protrusion 172 is disposed outwardly from the midline 170, or more than half of the distance of the inner edge 166 to the outer edge 168.

Furthermore, in the example of FIG. 5, the outermost portions of the protrusions are disposed toward the outer edge 168 more than 80% of the distance from the sleeve axis 158 to the outer edge 168, and in some embodiments, more than 90% of the distance from the sleeve axis to the outer edge 168.

The sleeve shank 154 extends from the proximally facing surface 162 (FIG. 3) of the head 152 and includes a transverse through hole 174 in each side sized to receive a pin (not shown) connecting the sleeve 120 and driving shaft 118. When assembled with the driving shaft 118, the hole 174 aligns with the slot 150 in the driving shaft 118 for slidable, pinned attachment.

Referring now to FIG. 3, as can be seen, the distally facing blade contacting surface 160 of the sleeve 120 and the blade contacting surface 130 of the driving shaft 118 face each other. The pieces may axially move apart to receive the blade 104, and then come together to clamp the blade 104 between the blade contacting surfaces. When assembled, the shaft axis 127 (FIG. 4) of the driving shaft 118 and the sleeve axis 158 (FIG. 5) of the sleeve are co-axially aligned with the longitudinal collet axis 122 (FIG. 3). These form a centerline about which the saw blade 104 can oscillate. The protrusions 172 (not shown for clarity in FIG. 3) extending from the distally facing blade contacting surface 160 fit within the receiving recess 140 formed in the head of the driving shaft 118 to both secure and align the saw blade 104, as discussed below.

Here, the receiving recess 140 is shown as a single groove formed radially about the shaft axis 127, and extending into the proximally facing blade contacting surface 130. In some embodiments, the collet assembly 116 includes no receiving recess, but the protrusions extend to and abut directly against the substantially planar proximally facing blade contacting surface 130.

Figure 6:
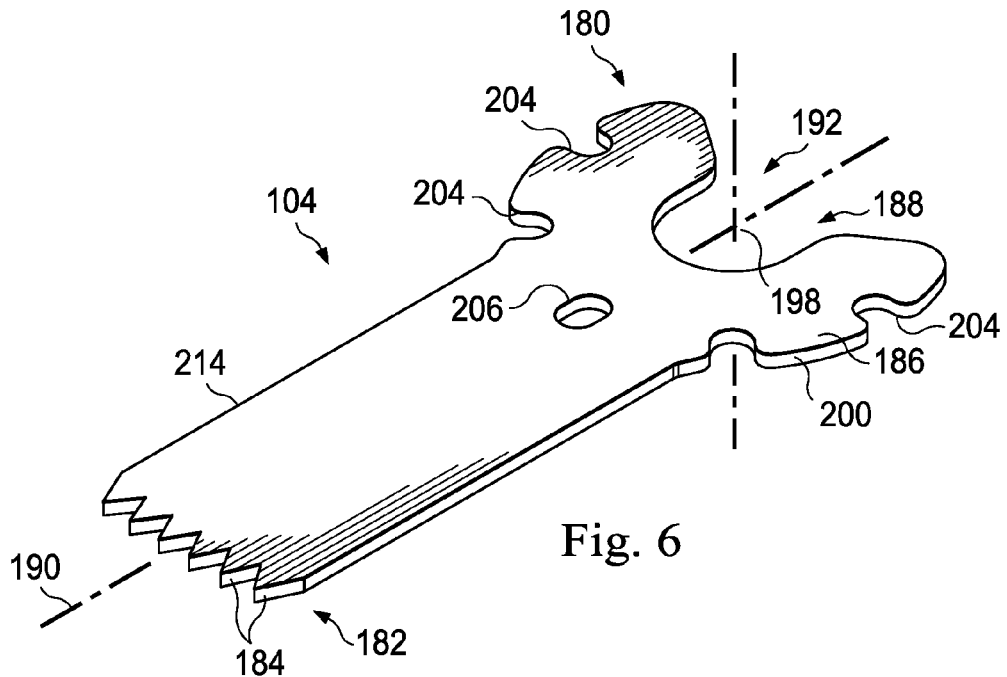
FIGS. 6 and 7 are illustrations of an exemplary micro-saw blade of the bone cutting surgical system of FIG. 1.
Figure 7:
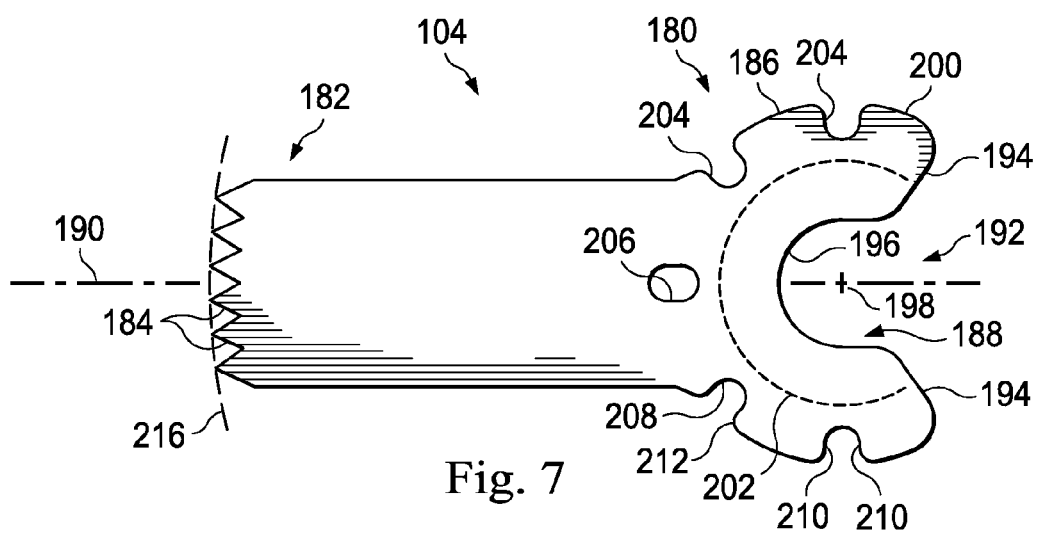

FIGS. 6 and 7 show the exemplary micro-saw blade 104 usable with the surgical saw 102 in FIG. 1 and securable with the collet assembly 116 in FIGS. 2-5. The micro-saw blade 104 includes a proximal end 180 that that facilitates interconnection with the collet assembly 116 and a distal end 182 having a cutting edge including a plurality of cutting teeth 184 formed thereon.

In this example, the proximal end 180 is defined by a relatively bulbous head 186 that includes a slot 188 extending inwardly along a longitudinal axis 190 form the proximal end of the saw blade 104. The slot 188 is formed with a funnel-like opening 192 defined by substantially straight edges 194 facing toward the longitudinal axis 190. The straight edges may help guide the saw blade 104 into place on the collet assembly, and form an angle between 70 and 160 degrees, but more particularly, within a range of about 90 to 120 degrees. The slot 188 also includes a slot edge 196 shaped to interface with the blade receiving groove 146 on the driving shaft 118 (FIG. 3). Because the blade receiving groove 146 is cylindrically shaped, the slot edge 196 is formed as a semi-circle, about a center point 198 defined by the bulbous head 186, with substantially parallel sides extending proximally from the slot edge toward the funnel-like opening 192. The slot edge 196 at least in part defines an inner edge of the bulbous head 186. A partially circular outer perimeter 200, which in this embodiment is concentric with the slot edge 196, defines an outer edge of the bulbous head 188. In some embodiments, the outer perimeter 200 has a diameter substantially the same as, or slightly smaller than, the diameter of the driving shaft head 124 and the sleeve head 152. For reference, a concentric midline 202 splits the distance between the outer perimeter 200 and the slot edge 196 in FIG. 7.

Openings 204 formed in the outer perimeter 200 and extending through the blade 104 permit the saw blade 104 to be secured to the surgical saw collet assembly 116. In the embodiment shown, the openings 204 are symmetrically disposed about the center point 198. Here, at least two openings 204 lie directly on opposing sides of the center point and on transverse sides of the longitudinal axis 190. A centrally disposed opening 206 lies along the longitudinal axis 190. The central opening 206 is spaced the same distance from the center point 198 as the perimeter openings 204. In the example shown the openings 204, 206 are offset from each other by 45 degrees and are sized to match the protrusions 172 on the distally facing surface of the sleeve 120. However, other offset angles are contemplated that match the desired collet assembly.

The openings 204, 206 are disposed offset from the midline 202 defined by the outer perimeter 200 and the slot edge 196 of the bulbous head 186. In the example shown, the openings 204, 206 are formed so that innermost edge portions (edge portions closest to the centerpoint 198) are disposed closer to the outer perimeter 200 than to the slot edge 196. Accordingly, the innermost edge of the opening is spaced from the slot edge 196 more than half of the distance between the outer perimeter 200 and the slot edge 196. In some embodiments, the innermost edge portions of the openings 204, 206 are spaced toward the perimeter edge to be more than about 70% of the distance between the outer perimeter 200 and the slot edge.

Furthermore, as measured from the centerpoint 198, the innermost edge portions of the openings may be located toward the outer perimeter 200 more than 80% of the distance between the perimeter 200 and the centerpoint 198, and in other embodiments, more than 90% of the distance between the perimeter 200 and the centerpoint 198.

Each opening 204, 206 is shaped to be slot-like, having a semi-circular inner end 208 and substantially parallel sides 210, albeit for a relatively short distance, extending from the semi-circular end 208 toward the outer perimeter 200. Chamfered or rounded edges 212 smooth the transition from the opening 204 to the outer perimeter 200. This reduces the chance of snagging or perforating surgical gloves on the proximal end 180 of the saw blade 104. This is particularly useful because the outer perimeter 200 may be closely aligned with, or slightly smaller than the outer perimeters of the heads of the driving shaft and sleeve. It is noted that the transition from the outer perimeter 200 to the straight edges 194 of the slot opening 192 are also chamfered or rounded.

In the example shown, the bulbous head 186 includes five openings 204, 206. However, in other embodiments, more or less openings may be provided. When the funnel-like opening 192 has an angle smaller than that shown, additional openings may be included, while maintaining the 45 degree spacing shown.

The saw blade 104 includes a shank 214 interposed between the proximal end 180 and the distal end 182. The distal end 182 of the saw blade 104 includes the plurality of teeth 184 formed at angles of 60 degrees, however, other angles, both larger and smaller are contemplated. The cutting teeth angle may be at least partially dependent on the surgical application. In the embodiment shown, tips of the teeth are formed so that together, the teeth define a circular path, indicated by the reference line 216.

Figure 8:
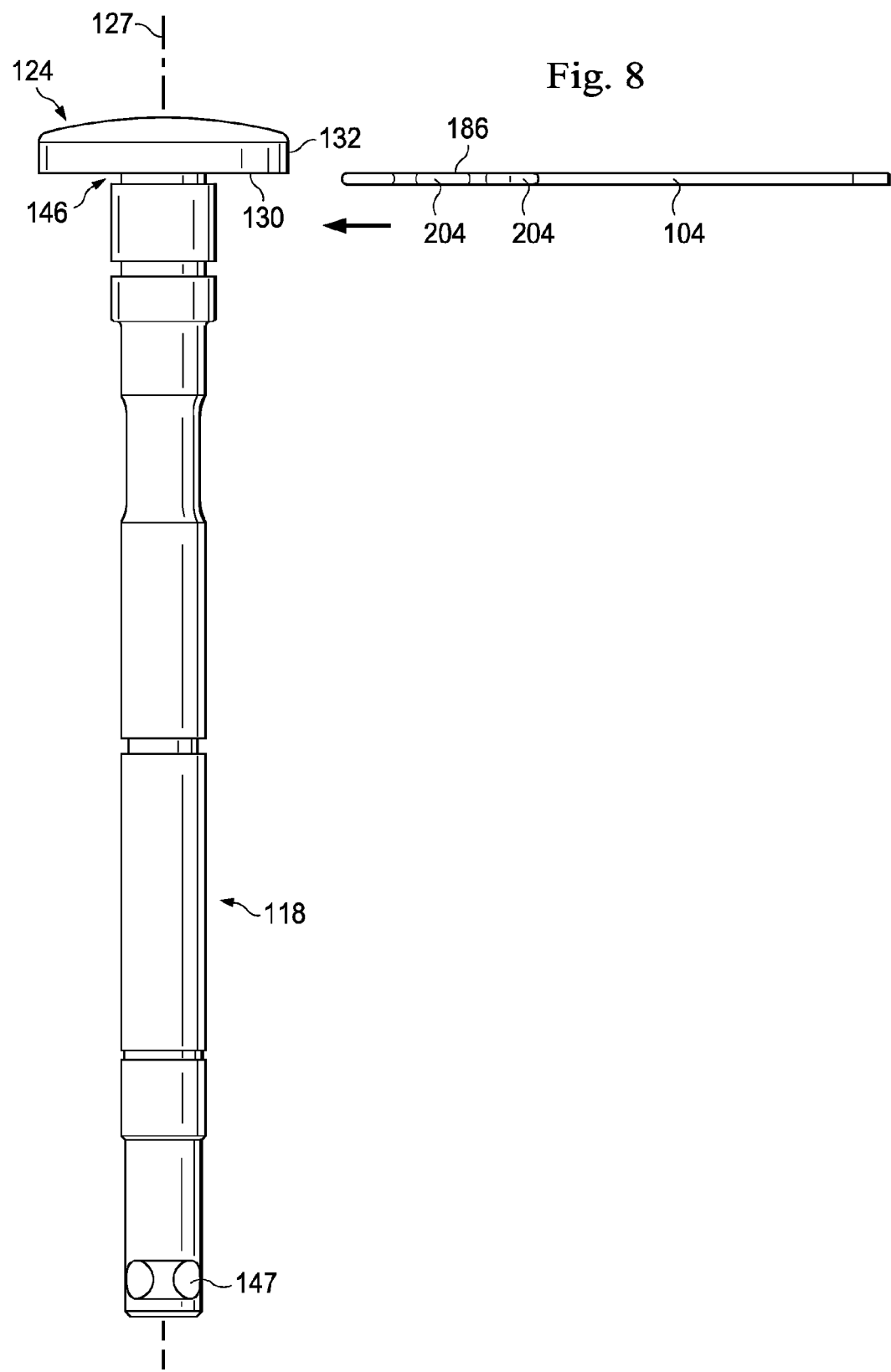
FIG. 8 is an illustration of the driving shaft of FIG. 3 with a micro-saw blade.
Figure 9:
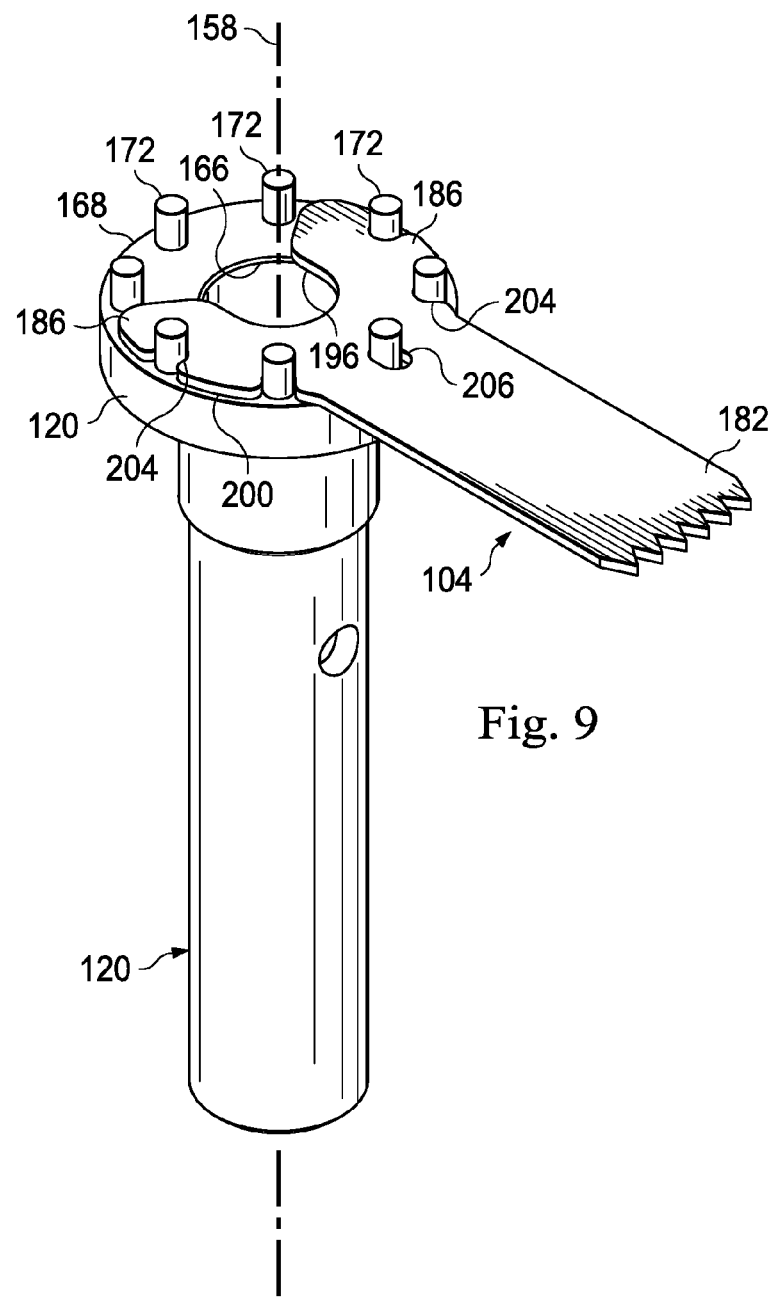
FIG. 9 is an illustration of the sleeve of FIG. 4 with an in-place micro-saw blade.

FIGS. 8 and 9 respectively show the blade 104 with reference to the driving shaft 118 and the sleeve 104, respectively. Although the blade 104 is shown separately with respect to each of the shaft and sleeve, when the driving shaft 118 and the sleeve 104 are joined together to form the collet assembly 116, it is contemplated that a single blade will be used at a time, although other arrangements are possible. First, with reference to FIG. 8, the bulbous head 186 of the blade 104 fits partially within the blade receiving groove 146. In order to provide a secure fit, the slot 188 (FIG. 7) is formed with a diameter that easily receives the inner portion of the receiving groove 146, but also has a clearance close enough to provide some stabilizing support to the blade 104. The bulbous head 186 of the saw blade 104 is substantially the same size or slightly smaller than as the outer perimeter of the head of the driving shaft. It should be noted that when the blade 104 is properly received in the receiving groove 146, the center point 198 of the blade 104 is aligned with the shaft axis 127, such that the outer perimeter 200 of the blade 104 and the outer perimeter 132 of the shaft head 124 are concentric. During assembly, the blade 104 is first introduced into the receiving groove 146 adjacent the blade contacting surface 130 of the shaft head 124 so that the bulbous head 186 lies flush with the blade contacting surface 130, as indicated by the arrow. The sleeve 120 is then axially slid along the shaft 118 so that the protrusions 172 (not shown in FIG. 8) engage the openings 104, 106 in the blade 104.

FIG. 9 shows the protrusions 172 of the sleeve 120 interfacing with the openings 204, 206 on the bulbous head 186 of the micro-saw blade 104, without the driving shaft 118. In some embodiments, when assembled with the driving shaft 118, the protrusions 172 extend through the openings 204, 206 and extend at least partially into the receiving recess 140 on the driving shaft 116 (FIG. 3). In other embodiments, the protrusions 172 have a length substantially the same as the thickness of the bulbous blade head 186 such that the protrusions just abut against or lie substantially flush with the proximally facing blade contacting surface 130 of the driving shaft 118 (FIG. 4).

In the example shown, the saw blade 104 has only five openings and receives five protrusions 172. In other embodiments, the saw blade 104 has more or fewer openings that receive the protrusions. In one example, the blade 104 includes seven openings and receives seven protrusions. Because the protrusions are spaced 45 degrees apart, the blade 104 can be removed and secured onto the sleeve in eight different positions. In some embodiments, for example, the sleeve includes only four protrusions or six protrusions, and the openings on the blade 104 are chosen to correspond with the protrusions.

It should be noted that when the blade 104 is properly disposed on the sleeve 120, the center point 198 of the blade 104 aligns with the sleeve axis 158, such that the outer perimeter 200 of the blade 104 and the outer perimeter 164 of the head of the sleeve 120 are concentric.

Because the sleeve protrusions 172 are disposed closer to the outer edge 168 than the inner edge 166, and likewise, because the blade openings 204 are disposed closer to the perimeter 200 than the slot edge 196, the protrusions 172 provide a longer moment arm than conventional systems, thereby providing higher torque with the same forces. This in turn increases the torque at the distal end 182 of the saw blade 104, permitting an equivalent torque while reducing the motor force, or alternatively, using the same motor force to provide increased cutting force. In addition, by increasing the distance of the moment arm from the blade centerpoint to the protrusions, there is less moment placed on the interior portions of the blade when it is oscillating. This may reduce vibration that might otherwise occur, in turn potentially reducing the amount of play and increasing accuracy achievable with the cutting blade 104. By providing openings 204, 206 on the blade 104 relatively far from the centerpoint of the shaft, the moment force at the distal end 182 of the blade 104 may be maximized.

Figure 10:
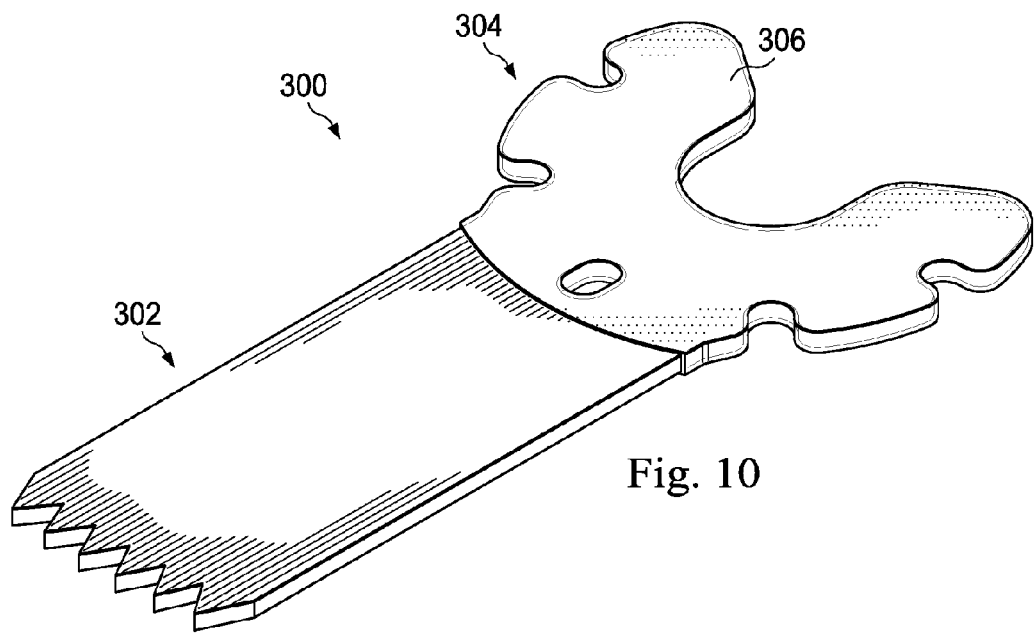
FIGS. 10-12 are illustrations of additional exemplary micro-saw blades usable with the bone-cutting surgical system.

FIG. 10 shows an alternative embodiment of a micro-saw blade, referenced by the reference numeral 300. Many of the features of the micro-saw blade 300 are similar to those of the micro-saw blade 104 discussed previously. Accordingly, only the differences are addressed in detail here. Here, the saw blade 300 is formed of a first material such as a single stamped material that provides the distal cutting end 302, and also formed of a second material different than the first material that forms at least a part of the proximal end 304. In this example, in addition to forming the distal end 302, the first material forms a part of a bulbous head section 306. The second material is overmolded about the first material to also form a part of the bulbous head section 306. In some examples the second material at the bulbous head section 306 is formed of a material more compliant than the blade material. In some examples, the overmold is a polymer material molded over a cutting blade portion formed of a surgical steel. Some examples of materials for the overmold include, for example, biocompatible low density polyethylene or polypropylene. Other examples are formed of elastomers, including blends to achieve a desired strength or durability. However, any biocompatible material may be used.

As shown in FIG. 10, the overmold material is formed to have substantially the same profile as the cutting blade so that the protrusions on the collet assembly will securely attach the cutting blade 300 in the same manner as the cutting blade 104. Furthermore, during use, the overmold material provides some dampening and cushioning to the saw blade 300. This dampening may reduce vibration experienced by the surgeon, providing some relief to hand and arm fatigue, and also decreasing blade wobble, increasing accuracy of the cut. The overmold also provides additional protection to the surgeons fingers and surgical gloves, as the overmold may provide additional protection from sharp or rigid edges that may be located about the proximal end 304 of the saw blade 300.

Figure 11:
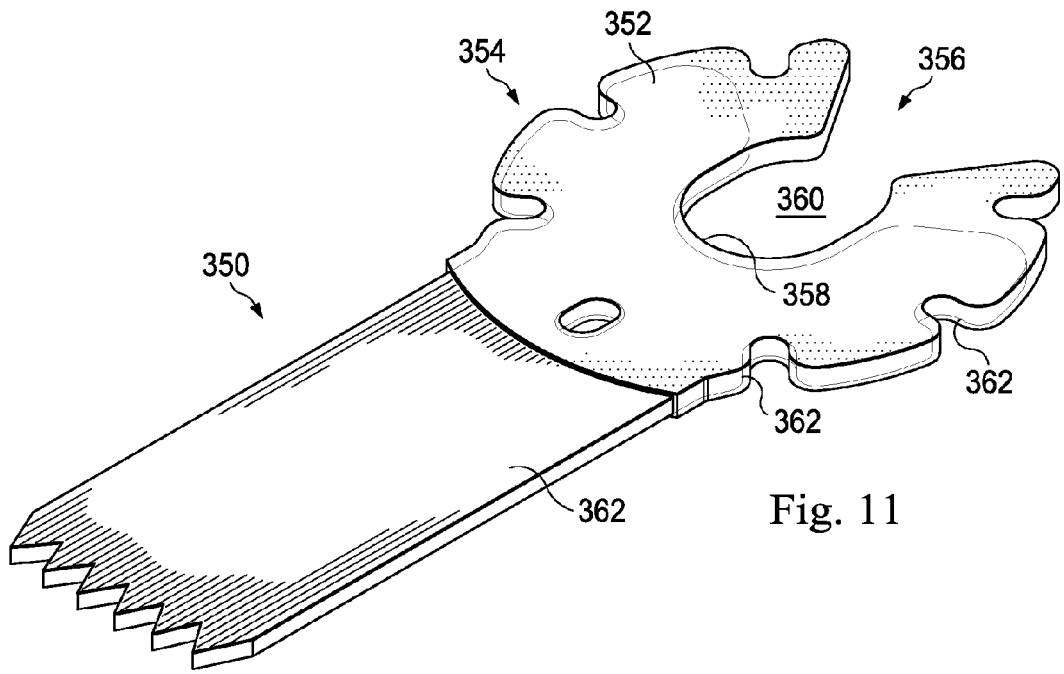

In the embodiment shown, the saw blade 300 may be secured to the sleeve 120 discussed above by five protrusions 172 out of eight since the most proximal portion of the bulbous head 306 forms the tapering opening. However, in an alternative embodiment, shown in FIG. 11, a saw blade referenced herein as 350 includes an overmold 352 forming a part of the bulbous head 354 that extends further around a slot opening 356, thereby at least partially enclosing an inner end 358 of the slot 360 in the saw blade 350. The slot 360 in the center of bulbous head 354 still receives the shank of the driving shaft 118. As shown in FIG. 11, while a blade portion 362 of the saw blade 350 appears to have a size substantially as discussed above, the overmold 352 itself extends about further, partially enclosing the slot 360. This overmold 352 deforms when the saw blade 350 is attached or detached from the collet assembly 116 to permit the shank 126 of the driving shaft 118 to enter the slot 360. In another embodiment, the overmold 352 completely encloses the slot 360 to hold the blade 350 in place by extending a full 360 degrees around the shank 126 of the driving shaft 118.

The overmolded portion in FIG. 11, like the overmolded portion in FIG. 10, contains openings 362 that match the raised protrusions in the collet assembly. With this over molded plastic arrangement, the blade 350 receives seven or in some embodiments, eight of the protrusions 172. The collet assembly holds the blade 350 in place, yet the pliable and deformable overmold permits easy blade removable. Further, the increased contact provided by the additional material helps further frictionally secure the blade in place and may provide surgeons with more control for precise cuts.

Figure 12:
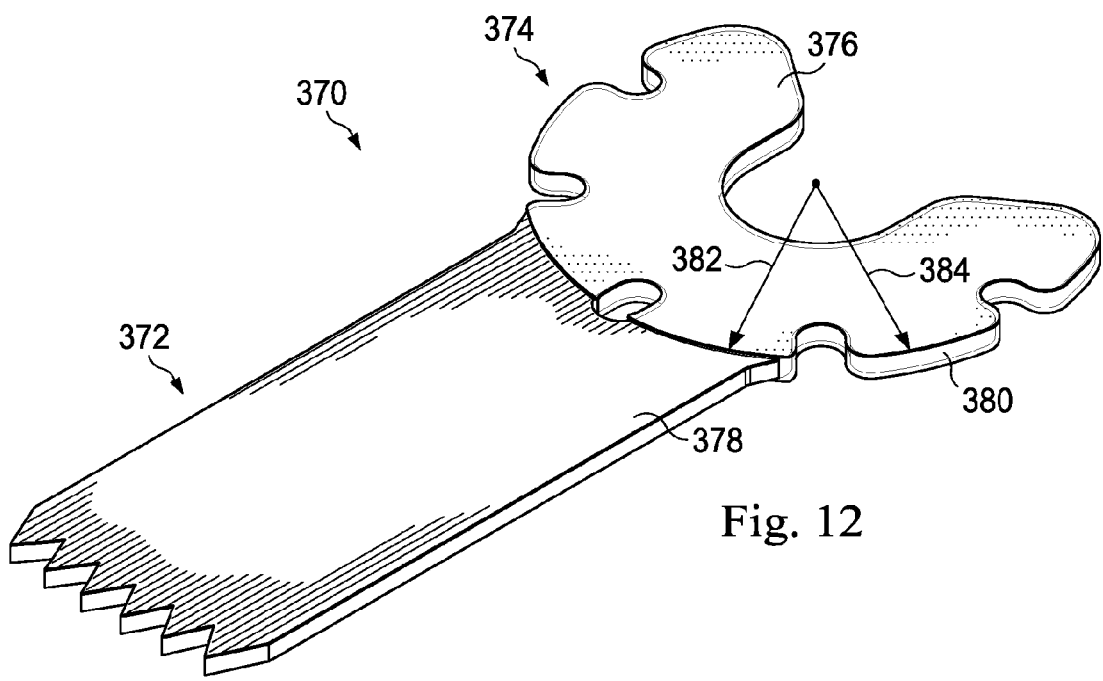

FIG. 12 shows an additional embodiment of an exemplary saw blade, referenced herein by the numeral 370. Here, the saw blade 370, like the saw blade 300 discussed above, includes a distal cutting end 372, a proximal end 374, and a bulbous head section 376. For reference, FIG. 12 identifies a shank 378 and an outer perimeter 380 of the bulbous head 376. The second material is overmolded about the first material to also form a part of the bulbous head 376. Here, the second material is formed on the blade 370 to cover primarily just the bulbous head section 376. Because of this, the second material does not extend down the shank 378 toward the distal end 372, but has a radius 382 that substantially matches the radius 384 of the outer perimeter 380 of the bulbous head 376. Accordingly, when placed in the collet assembly 116, the second material is substantially contained between the two blade contacting surfaces, with only the shank extending outwardly from the collet assembly 116.

The overmold in FIGS. 10-12 may be formed of a material softer than the sleeve 120 and driving shaft 118 materials. Accordingly, the overmold may reduce friction wear on the sleeve 120 and driving shaft 118 by yielding before the harder materials wear. Because the sleeve 120 and driving shaft 118 of the collet assembly 116 may be more expensive to manufacture than the saw blades, preserving the collet assembly may be beneficial to customers and may prolong the useful life of the associated surgical saw.

In one embodiment, the overmold is colored to provide information to a surgeon regarding, for example, a blade size, tooth type, or blade thickness. For example, a saw blade having a thickness of 0.010 inch includes a blue overmold and a blade having a thickness of 0.15 includes a red overmold. Accordingly, in some instances, a surgeon may select a desired blade from a blade set of a plurality of blades, with each blade having a colored overmold corresponding to a specific thickness, size, or tooth type.

Figure 13:
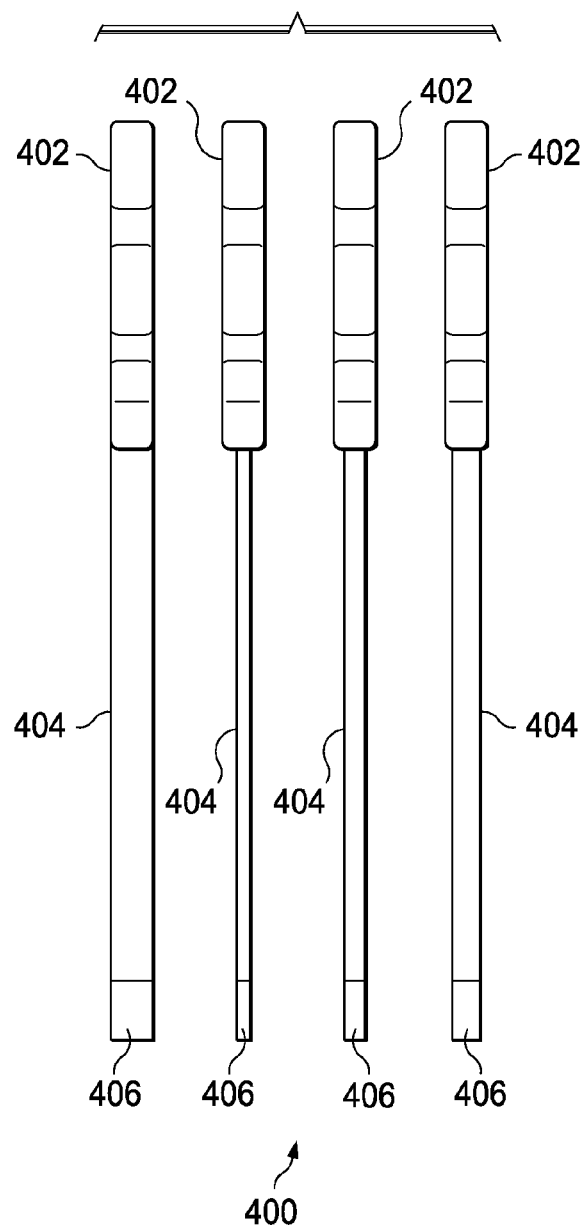
FIG. 13 is an illustration of an exemplary blade set having a plurality of micro-saw blades.

FIG. 13 shows a side view of an exemplary blade set 400 usable with the collet assembly 116 disclosed herein. Each blade of the blade set 400 includes a proximal end 402 formed of a bulbous head, a shank 404, and distal cutting end 406. In this embodiment, however, the proximal end 402 of each blade of the blade set 400 has the same thickness, but the thicknesses of the shanks 404 and cutting edges 406 varies. Because the proximal end 402 has the same thickness, the head of each of the blades of the set fits within the receiving groove 146 on the shank 126 of the driving shaft 118 with the same amount of clearance or play for consistency and repeatability. Yet the blade shank 404 and distal cutting edge 406 vary so that a surgeon may select a blade with the desired thickness for the particular surgical application. For example, some blade sets may include blades that vary in thickness between 0.007 and 0.027 inch. The thickness of the proximal end 402 may be a result of an overmold as described above with respect to FIGS. 10 and 11, or alternatively, may be laminated or integrally formed of a single monolithic material. In this blade set 400, colored overmolding may identify the thickness of each cutting blade to permit a surgeon to distinguish one blade from another.

Figure 14:
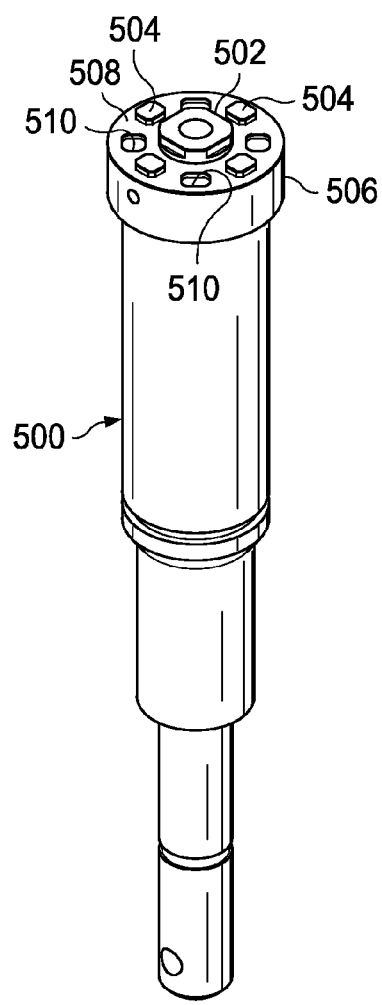
FIGS. 14 and 15 are illustrations of components of an alternative collet assembly.
Figure 15:
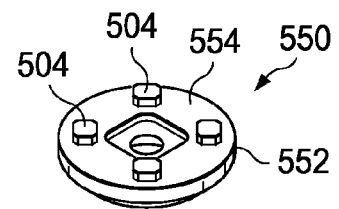

FIGS. 13 and 14 show components of an alternative collet assembly, with FIG. 14 showing an alternative sleeve 500 disposed about a shank 502 of a driving shaft, and with FIG. 15 showing a driving shaft head 550 separate from the shank 502. Protrusions 504 on the sleeve 500 and head 550 are spaced toward the respective perimeter edges 506, 552, in the manner discussed above. Accordingly, the description above regarding protrusion placement and placement of the receiving groove is equally applicable to the embodiment in FIGS. 13 and 14.

The sleeve in FIG. 14 includes a distally facing blade contacting surface 508 having both protrusions 504 and recessed receiving openings 510 spaced toward the perimeter edge 506 in the manner discussed above. In this embodiment, the protrusions 504 are rectangular or square rather than the cylindrical pins discussed above. It is contemplated that the driving shaft head 550 and the sleeve 500 would be used to secure a saw blade having corresponding shaped openings. In some embodiments, the protrusions or receiving openings are on the driving shaft, while in other embodiments, the sleeve includes some protrusions and the driving shaft includes other protrusions.

In FIG. 15, the head 550 is removable from the shank of the driving shaft, but may be attached using a fastener, such as a screw. The head 550 includes a proximally facing blade contacting surface 554 that includes protrusions 504 for engaging corresponding openings in a matching saw blade. In this embodiment, as described above, the protrusions 504 are spaced toward the outer perimeter edge.

Figure 16:
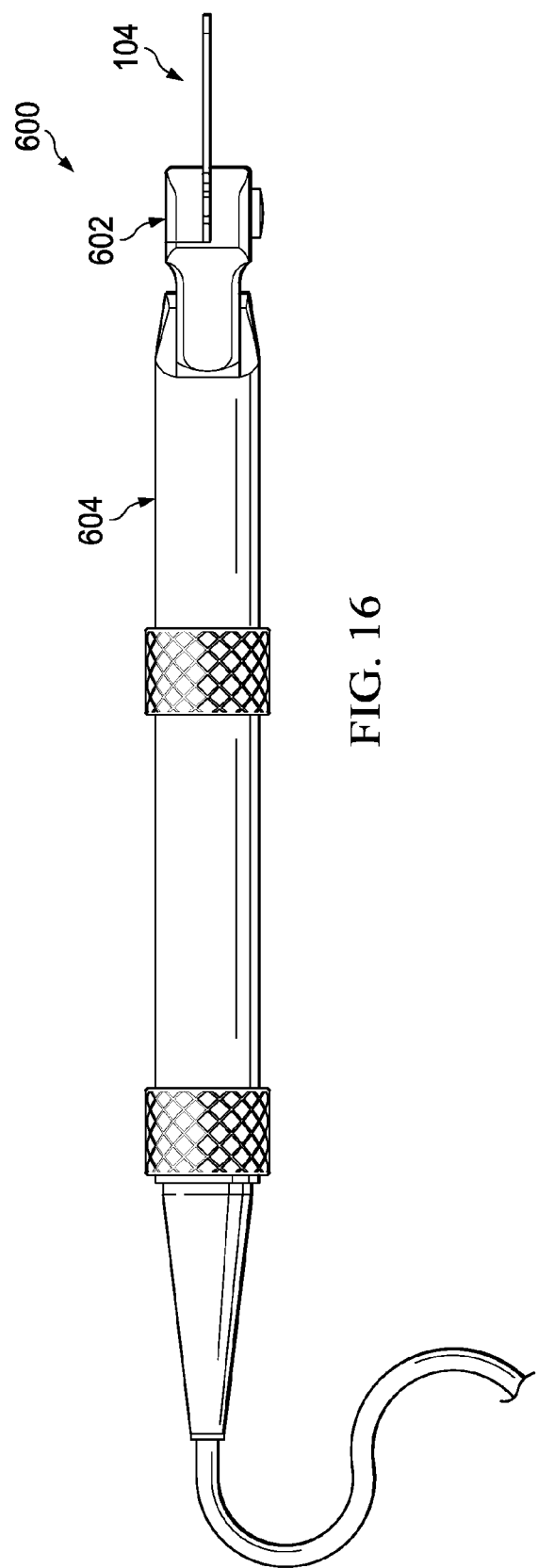
FIG. 16 is an illustration of an exemplary sagittal bone-cutting surgical system.

FIG. 16 shows a sagittal saw 600 for driving the saw blade 104. In this embodiment, the collet assembly 602 is arranged to secure the blade 104 in an axial direction relative to a saw handle 604. Accordingly, instead of having proximally and distally facing blade contacting surfaces, the collet assembly includes side-by-side blade contacting surfaces. However, like the oscillating saw 102 disclosed in FIGS. 1-6, the sagittal saw 600 includes protrusions disposed adjacent an exterior edge of the collet fixture, and the blade 104 is sized so that the outer perimeter of the head of the saw blade substantially corresponds to the edge of the collet assembly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A cutting blade set for cutting bone material when a blade is coupled to a surgical saw that is configured to selectively interface with each blade of the cutting blade set, the cutting blade set comprising:
a plurality of cutting blades, each blade of the plurality of cutting blades comprising:
a distal end comprising a plurality of cutting teeth, the distal end of each cutting blade of the plurality of cutting blades having a different thickness;
a shank portion adjacent the distal end; and
a proximal end adjacent the shank portion, the proximal end being sized and shaped to interface with the surgical saw, the proximal end of each cutting blade of the plurality of cutting blades having substantially the same thickness.

2. The cutting blade set of claim 1, wherein the proximal end of each of the plurality of cutting blades includes a portion formed of a first material and being overmolded with a second material having a hardness less than a hardness of the first material.

3. The cutting blade set of claim 1, wherein each of the plurality of blades includes openings in an outer perimeter configured to receive and interface with protrusions of the surgical saw in a manner that the protrusions cooperatively impart motion to drive the cutting blade.

4. The cutting blade set of claim 2, wherein the first material is a surgical steel and the second material is a polymer material.

5. The cutting blade set of claim 2, wherein each overmold of each cutting blade is colored with a different color to provide information to a surgeon.

6. The cutting blade set of claim 5, wherein the information includes blade size, tooth type, or blade thickness.

7. The cutting blade set of claim 2, wherein the proximal end formed of the first and second materials includes an upper substantially planar surface, a lower substantially planar surface and a side edge extending between the upper and lower planar surfaces, the side edge at least in part defining an outer perimeter extending about the proximal end, the outer perimeter including a plurality of indentations forming openings configured to receive and interface with protrusions of the surgical saw in a manner that the protrusions cooperatively impart motion to drive the cutting blade.

8. The cutting blade set of claim 2, wherein the proximal end defines a slot opening extending into the proximal end along a longitudinal axis of the cutting blade and formed into the first material, the second material being overmolded to either form a tapered opening into the slot opening, partially enclose an inner end of the slot opening, or completely enclose the slot opening.

9. The cutting blade set of claim 1, wherein the proximal end includes an upper substantially planar surface, a lower substantially planar surface and a side edge extending between the upper and lower planar surfaces, the side edge at least partially defining an outer perimeter extending about the proximal end, the outer perimeter including a plurality of indentations forming openings configured to receive and interface with protrusions of the surgical saw in a manner that the protrusions cooperatively impart motion to drive the cutting blade.

10. A cutting blade set for cutting bone material when a blade is coupled to a surgical saw that is configured to selectively interface with each blade of the cutting blade set, the cutting blade set comprising:
a plurality of cutting blades, each blade of the plurality of the cutting blades comprising:
a first material forming,
a distal end having a plurality of cutting teeth,
a shank portion adjacent the distal end, and
a proximal end adjacent the shank portion, the proximal end shaped to interface with the surgical saw; and
a second material overmolded at least over the proximal end of the first material, wherein each cutting blade of the plurality of cutting blades formed of the first material has a different thickness and each overmold of each cutting blade of the plurality of cutting blades have substantially the same thickness.

11. The cutting blade set of claim 10, wherein the second material has a hardness less than a hardness of the first material.

12. The cutting blade set of claim 11, wherein the first material is a steel and the second material is a polymer.

13. The cutting blade set of claim 10, wherein each cutting blade of the plurality of cutting blades includes openings in an outer perimeter configured to receive and interface with protrusions of the surgical saw in a manner that the protrusions cooperatively impart motion to drive the cutting blade.

14. The cutting blade set of claim 10, wherein each overmold of the second material is colored with a different color to provide information to a surgeon.

15. The cutting blade set of claim 10, wherein the proximal end includes an upper substantially planar surface, a lower substantially planar surface and a side edge extending between the upper and lower planar surfaces, the side edge at least in part defining an outer perimeter extending about the proximal end, the outer perimeter including a plurality of indentations forming openings configured to receive and interface with protrusions of the surgical saw in a manner that the protrusions cooperatively impart motion to drive the cutting blade.

16. The cutting blade set of claim 10, wherein the second material is overmolded over the proximal end and a portion of the shank portion.

17. The cutting blade set of claim 10, wherein the proximal end defines a slot opening extending into the proximal end along a longitudinal axis of the cutting blade and formed into the first material, the second material being overmolded to either form a tapered opening into the slot opening, partially enclose an inner end of the slot opening, or completely enclose the slot opening.

18. A cutting blade set for cutting bone material when a blade is coupled to a surgical saw that is configured to selectively interface with each blade of the cutting blade set, the cutting blade set comprising:

- a first cutting blade having a first distal end having a first thickness and a first plurality of cutting teeth,
- a first shank portion adjacent to the first distal end, and
- a first proximal end adjacent to the first shank portion having a second thickness, the first proximal end being sized and shaped to interface with the surgical saw; and
- a second cutting blade having a second distal end having a third thickness and a second plurality of the cutting teeth,
- a second shank portion adjacent the second distal end, and
- a second proximal end adjacent to the second shank portion having a fourth thickness, the second proximal end being sized and shaped to interface with the surgical saw;
- wherein the first and third thicknesses are different and the second and fourth thicknesses are the same.

19. The cutting blade set of claim 18, wherein the first proximal end and the second proximal end of the first cutting blade and the second cutting blade include a portion formed of a first material and being overmolded with a second material having a hardness less than a hardness of the first material.

20. The cutting blade set of claim 19, wherein the overmold of the first proximal end is a first color and the overmold of the second proximal end is a second color, the first color different from the second color, the first color corresponding to an indication of the first thickness and the second color corresponding to an indication of the third thickness.

* * * * *